(12) United States Patent
Sartor

(10) Patent No.: US 10,660,717 B2
(45) Date of Patent: May 26, 2020

(54) ROBOTIC INTERFACE POSITIONING DETERMINATION SYSTEMS AND METHODS

(71) Applicant: Covidien LP, Mansfield, MA (US)

(72) Inventor: Joe Sartor, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 298 days.

(21) Appl. No.: 15/306,119

(22) PCT Filed: Dec. 8, 2014

(86) PCT No.: PCT/US2014/069015
§ 371 (c)(1),
(2) Date: Oct. 24, 2016

(87) PCT Pub. No.: WO2015/163943
PCT Pub. Date: Oct. 29, 2015

(65) Prior Publication Data
US 2017/0042625 A1 Feb. 16, 2017

Related U.S. Application Data

(60) Provisional application No. 61/983,745, filed on Apr. 24, 2014.

(51) Int. Cl.
G05B 15/00 (2006.01)
G05B 19/00 (2006.01)
(Continued)

(52) U.S. Cl.
CPC .............. *A61B 34/37* (2016.02); *A61B 34/20* (2016.02); *A61B 34/74* (2016.02); *A61B 90/06* (2016.02);
(Continued)

(58) Field of Classification Search
CPC ......... A61B 34/37; A61B 90/06; A61B 34/20; A61B 34/74; A61B 34/30;
(Continued)

(56) References Cited

U.S. PATENT DOCUMENTS 6,364,888 B1  4/2002  Niemeyer et al.
6,747,632 B2  6/2004  Howard
(Continued)

FOREIGN PATENT DOCUMENTS

DE  102010009065 A1  8/2011
EP       2570890 A1  3/2013
(Continued)

OTHER PUBLICATIONS

Partial Supplementary European Search Report corresponding to counterpart Int'l Appln. No. EP 14 89 0236.4 dated Nov. 8, 2017.
(Continued)

*Primary Examiner* — Harry Y Oh

(57) ABSTRACT

The present disclosure is directed to a robotic surgical system that includes a robotic surgical device having a robotic arm and an end effector with a pair of jaw members. A handpiece includes a pinch interface to control the arm or end effector, optical marker(s), an accelerometer, and a transmitter to transmit data from the pinch interface or accelerometer to the robotic surgical device. The system further includes a tracking system, to track the marker and provide a position or orientation of the handpiece. A processor receives: (i) the position or orientation of the handpiece from the tracking system; and (ii) the measured acceleration of the handpiece from the accelerometer. The processor integrates the measured acceleration to establish a second position beyond that of the tracking system. The
(Continued)

processor controls movement of the robotic arm and end effector based on the received data from the camera or the accelerometer.

16 Claims, 6 Drawing Sheets

(51) Int. Cl.
 A61B 34/37 (2016.01)
 B25J 13/02 (2006.01)
 B25J 9/16 (2006.01)
 A61B 34/00 (2016.01)
 G06F 3/03 (2006.01)
 G06F 3/0346 (2013.01)
 A61B 34/20 (2016.01)
 A61B 90/00 (2016.01)
 A61B 34/30 (2016.01)

(52) U.S. Cl.
 CPC ............. *B25J 9/1689* (2013.01); *B25J 13/02* (2013.01); *G06F 3/0304* (2013.01); *G06F 3/0346* (2013.01); *A61B 34/30* (2016.02); *A61B 2034/2046* (2016.02); *A61B 2034/2048* (2016.02); *A61B 2034/2055* (2016.02); *A61B 2034/2059* (2016.02); *A61B 2090/064* (2016.02); *A61B 2090/067* (2016.02); *G05B 2219/40132* (2013.01)

(58) Field of Classification Search
 CPC ...... A61B 2090/064; A61B 2034/2055; A61B 2034/2048; B25J 9/1689; B25J 13/02; G05B 2219/40132
 See application file for complete search history.

(56) References Cited

U.S. PATENT DOCUMENTS

| 7,391,177 | B2 | 6/2008 | Kishi et al. | |
| 7,559,931 | B2 | 7/2009 | Stone | |
| 8,396,598 | B2 | 3/2013 | Sutherland et al. | |
| 8,600,674 | B1* | 12/2013 | Barbeau | H04W 4/029 701/524 |
| 8,812,160 | B2 | 8/2014 | Hagn et al. | |
| 9,361,818 | B2 | 6/2016 | Ogawa et al. | |
| 2001/0020200 | A1* | 9/2001 | Das | B25J 9/1689 700/260 |
| 2005/0181803 | A1* | 8/2005 | Weaver | H04W 4/029 455/456.1 |
| 2009/0308603 | A1* | 12/2009 | Borgstadt | B25J 9/1664 166/250.15 |
| 2011/0034921 | A1 | 2/2011 | Sartor | |
| 2011/0118748 | A1* | 5/2011 | Itkowitz | A61B 34/30 606/130 |
| 2012/0316681 | A1* | 12/2012 | Hagn | G06F 3/014 700/258 |
| 2013/0063580 | A1 | 3/2013 | Ogawa et al. | |
| 2013/0073088 | A1* | 3/2013 | Lee | G05D 1/0225 700/259 |
| 2013/0120141 | A1 | 5/2013 | Scalisi et al. | |
| 2014/0148819 | A1 | 5/2014 | Inoue et al. | |
| 2015/0141981 | A1* | 5/2015 | Price | A61B 18/1445 606/38 |

FOREIGN PATENT DOCUMENTS

| JP | 7194609 | | 8/1995 |
| JP | 2012071406 | A | 4/2012 |
| JP | 2012171088 | A | 9/2012 |
| JP | 2013510673 | A | 3/2013 |
| WO | 2012044334 | A2 | 4/2012 |

OTHER PUBLICATIONS

Chinese First Office Action corresponding to counterpart Patent Application CN 201480078205 dated Jul. 19, 2018.
Japanese Office Action corresponding to counterpart Patent Appln. JP 2016-564007 dated Sep. 18, 2018.
International Search Report for (PCT/US2014/069015) date of completion is Mar. 12, 2015 (5 pages).
Extended European Search Report corresponding to counterpart EP Patent Appln. 14 89 0236.4 dated Feb. 23, 2018.

* cited by examiner

ROBOTIC INTERFACE POSITIONING DETERMINATION SYSTEMS AND METHODS

CROSS-REFERENCE TO RELATED APPLICATIONS

This application is a U.S. National Stage Application filed under 35 U.S.C. § 371(a) of International Patent Application Serial No. PCT/US2014/069015, filed Dec. 8, 2014, which claims the benefit of U.S. Provisional Patent Application Ser. No. 61/983,745, filed Apr. 24, 2014, the entire disclosure of each of which are incorporated by reference herein.

BACKGROUND

1. Technical Field

The present disclosure relates to robotic surgical systems. Particularly, the present disclosure is directed to a hand-held user interface for controlling a robotic surgical system.

2. Background of the Related Art

Robotic surgical systems have been used in minimally invasive medical procedures. Some robotic surgical systems included a console supporting a robot arm and a surgical instrument or end effector, such as forceps or a grasping tool, mounted to the robot arm. A mechanical input device having multiple joints was manipulated by surgeons to move the robot arm and/or surgical instrument mounted to the robot arm.

The mechanical input device offered a limited range of motion in which the device could be moved that varied depending on the configuration of joints and rods connecting the joints. Larger ranges of motion were achieved by enlarging the joints and/or rods to increase workspace in which the input device moved and/or upscaling the output motion of the end effector. Enlarging the joints, rods, and/or workspace made the system less easily transportable. Upscaling the end effector motion reduced the precision of micro-movements of the end effector from ergonomically scaled motions of the input device, making the system less precise.

The size of the robotic system and input device may be reduced by using a wireless input device with optical tracking technology, such as light sources and position sensitive detectors, instead of a mechanical input device. While an optical input device would eliminate space requirements of the mechanical rods and joints, the range of motion would still be limited by the properties and configuration of the position detectors and the light sources. Larger ranges of motion were also supported by upscaling the end effector motion and thereby reducing the precision of the surgical system.

There is a need for easily transportable surgical robot input devices having a larger range of motion that also occupy a smaller footprint. There is also a need for optical tracking input devices supporting a larger range of motion that do not reduce the precision of end effector movements through upscaling.

SUMMARY

Robotic surgical systems may be programmed with additional instructions and include additional non-optical sensors that supplement optical tracking sensors in the input device. The additional non-optical sensors may be configured to provide an additional range of motion for the input device that exceeds the range of motion of the optical tracking sensors. The additional programming instructions may include algorithms that reduce position calculation errors between the signals obtained from the optical and non-optical sensors. These algorithms may also provide for a smoother transition when changing the input source of the positional calculations between the optical and the non-optical sensors.

A robotic surgical system may include a robotic surgical device having at least one robotic arm and an end effector having a pair of jaw members at a distal end of the robotic arm. The system also includes an operating console. A handpiece includes a pinch interface configured to control the end effector on the robotic surgical device, at least one marker, an accelerometer configured to measure acceleration of the handpiece, and a transmitter configured to transmit data from at least one of the pinch interface or accelerometer to the robotic surgical device. The system also includes a tracking system that tracks the marker and provides a position or orientation of the handpiece. A controller receives the position or orientation of the handpiece from the tracking system or the measured acceleration of the handpiece from the accelerometer. The controller controls the movement of the robotic arm based on the position, the orientation, or the acceleration of the handpiece.

The pinch interface may include a pair of pinch members. In some aspects, the pair of pinch members may include at least one pinch sensor configured to measure relative movement of the pinch members. The relative movement of the pair of pinch members causes the pair of jaw members to move. The measured relative movement of the pair of pinch members is multiplied by a predetermined factor to cause movement of the pair of jaw members.

In some aspects, the pair of pinch members may include a force sensor to measure a force applied to the pair of pinch members. The force applied to the pair of pinch members causes the pair of jaw members to move to a position at which a closure force to tissue disposed between the pair of jaw members is proportionally matched to the pinch members.

The robotic surgical device may include a plurality of robotic arms and the handpiece may include a switch configured to select one of the robotic arms.

In other aspects, the handpiece may include a switch configured to engage a master device or a slave device.

In aspects the tracking system is an optical, a magnetic, or an inductive tracking system.

In another aspect of the present disclosure, a hand-held instrument for controlling a robotic surgical device is provided. The hand-held instrument includes at least one handpiece that has a pinch interface configured to control an end effector on a robotic surgical device and an accelerometer configured to measure acceleration of the handpiece. The handpiece also includes a transmitter configured to transmit data from at least one of the pinch interface or the accelerometer to a robotic surgical device to control movement of a robotic surgical device.

In yet another aspect of the present disclosure, a method for controlling a robotic surgical device using a hand-held interface is provided. The method includes capturing an image of a plurality of optical markers on the hand-held interface. A position or orientation of the hand-held interface is determined based on the image. Acceleration data is received from the hand-held interface. Movement of the robotic surgical device is controlled based on the determined position or orientation of the hand-held interface or the acceleration data of the hand-held interface.

A position or orientation of the robotic surgical device may be controlled based on the determined position or orientation of the hand-held interface. The position or orientation of the robotic surgical device may be controlled based on the acceleration data when the position and orientation of the hand-held interface cannot be determined. The acceleration data may be used to calculate an estimated position or orientation of the robotic surgical device.

In some aspects, determining the position or orientation of the hand-held interface includes comparing the captured image to a database of images. In other aspects, determining the position or orientation of the hand-held interface includes calculating at least two distances between at least two of the optical markers.

In some aspects, position of the handpiece is brought back into alignment when the handpiece is again locatable by the optical markers determined orientation by adjusting a non-zero velocity movement of the robot.

In another aspect of the present disclosure, a method of reorienting a hand-held interface with a robotic surgical device having an end effector is provided. The method includes detecting the hand-held interface in a working field and establishing an absolute position and angular errors of the hand-held interface to the end effector. Movement of the hand-held interface is detected and a positional or angular velocity offset of the hand-held interface is calculated. The vector of the hand-held interface near a current vector of movement relative to the end effector is aligned based on the calculated positional or angular velocity offset of the hand-held interface.

The calculated positional or angular velocity offset may be a fractional multiplier of a velocity of the hand-held interface. A magnitude of the fractional multiplier may be derived from a magnitude of an offset in an orientation of the movement and a scaling factor. The scaling factor may be a non-dimensional factor, an angular factor, a dimensional factor, or a time factor.

Further details and aspects of the present disclosure are described in more detail below with reference to the appended figures.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
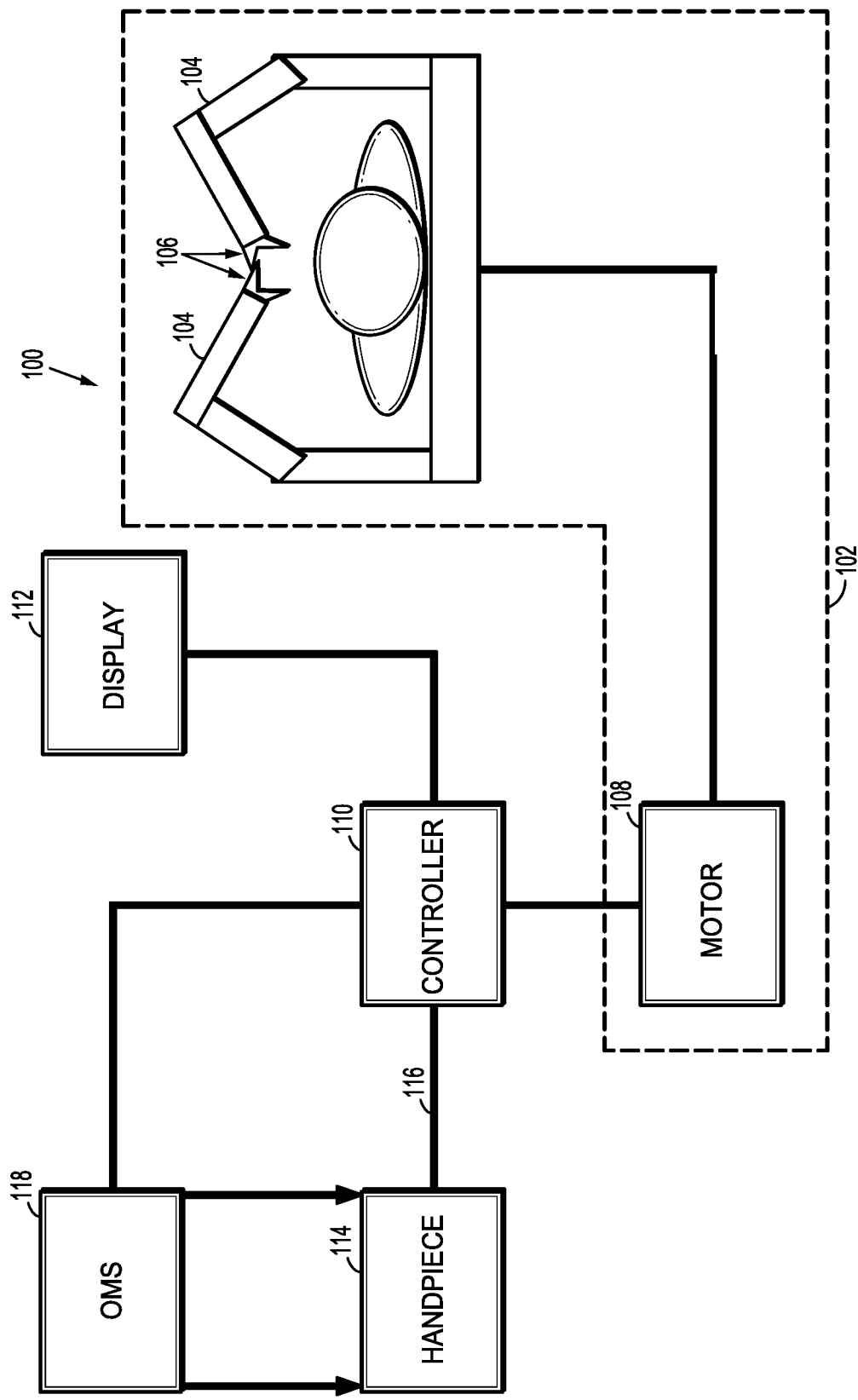
FIG. 1 is a schematic illustration of a robotic surgical system in accordance with an embodiment of the present disclosure.

Particular embodiments of the present disclosure are described herein with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A or B" means "(A), (B), or (A and B)". For the purposes of this description, a phrase in the form "at least one of A, B, or C" means "(A), (B), (C), (A and B), (A and C), (B and C), or (A, B and C)".

The term "clinician" refers to any medical professional (i.e., doctor, surgeon, nurse, or the like) performing a medical procedure involving the use of embodiments described herein. As shown in the drawings and described throughout the following description, as is traditional when referring to relative positioning on a surgical instrument, the term "proximal" or "trailing" refers to the end of the apparatus which is closer to the clinician and the term "distal" or "leading" refers to the end of the apparatus which is further away from the clinician.

The systems described herein may also utilize one or more controllers to receive information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" is any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. For the purposes of this definition, no distinction is made between languages which are interpreted, compiled, or use both compiled and interpreted approaches. For the purposes of this definition, no distinction is made between compiled and source versions of a program. Thus, reference to a program, where the programming language could exist in more than one state (such as source, compiled, object, or linked) is a reference to any and all such states. The definition also encompasses the actual instructions and the intent of those instructions.

Any of the herein described methods, programs, algorithms or codes may be contained on one or more machine-readable media or memory. The term "memory" may include a mechanism that provides (e.g., stores and/or transmits) information in a form readable by a machine such as a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

A switch may include a device capable of effecting a change between at least two states. Thus, a switch may include a push button, toggle, transistor, rotary mechanism, scroll wheel, rocker, knife switch, and so on.

The present disclosure is directed to a hand-held interface or handpiece designed to be sterilized and enable a clinician to operate a robotic surgical system from within the sterile operating field. The clinician may have separate left and right handpieces. Each of the handpieces may contain finger pinch controls that include pinch sensors and force sensors. The handpieces are tracked in absolute space by positional sensor systems that are commonly used in operating rooms (e.g., an optical system). The handpieces of the present disclosure also incorporate a-axis accelerometers to provide redundant position or orientation information. The handpieces transmit data to a controller which controls the robotic surgical devices. The position of the handpiece is augmented using the accelerometer data when the optical systems are unable to track the handpiece (e.g., when a clinician obscures the view of any or all optical markers).

In some embodiments, magnetic field sensors that use coils in the handpiece may be used to track the handpiece via magnetic or inductive tracking systems.

Turning to FIG. 1, one example of a robotic surgical system in accordance with an embodiment of the present disclosure is shown generally as 100. The system 100 includes a robotic surgical device 102 that includes a plurality of robotic arms 104 having end effectors 106 and a motor 108 configured to control the plurality of robotic arms 104 and the end effectors 106. The end effectors 106 may be forceps (as shown in FIG. 1), probes, cameras, or any other instrument suitable for use in a surgical procedure. The robotic surgical device 102 is controlled by a controller 110. A display 112 provides a visual representation of a surgical field to the clinician. The display 112 may be a television or monitor that provides a two-dimensional or three-dimensional view of the surgical field. In some embodiments, the display 112 may be a pair of glasses that projects an image onto one of the lenses (e.g., GOOGLE GLASS®).

A handpiece 114 controls the robotic surgical device 102 by providing instructions to controller 110 via a transmission conduit 116. The transmission conduit 116 may be a wire, optical fiber, radio waves, or other wireless communication conduit. The system 100 may include a single handpiece 114 to control the robotic surgical device 102 or the system 100 may include two handpieces 114 (a left and a right handpiece). An optical measurement system (OMS) 118, which may include at least one image capturing device and a processor, is used to track a position or orientation of the handpiece 114. The OMS 118 may be, for example, the POLARIS SPECTRA® or the POLARIS VICRA® systems (manufactured by Northern Digital, Inc.).

Figure 2:
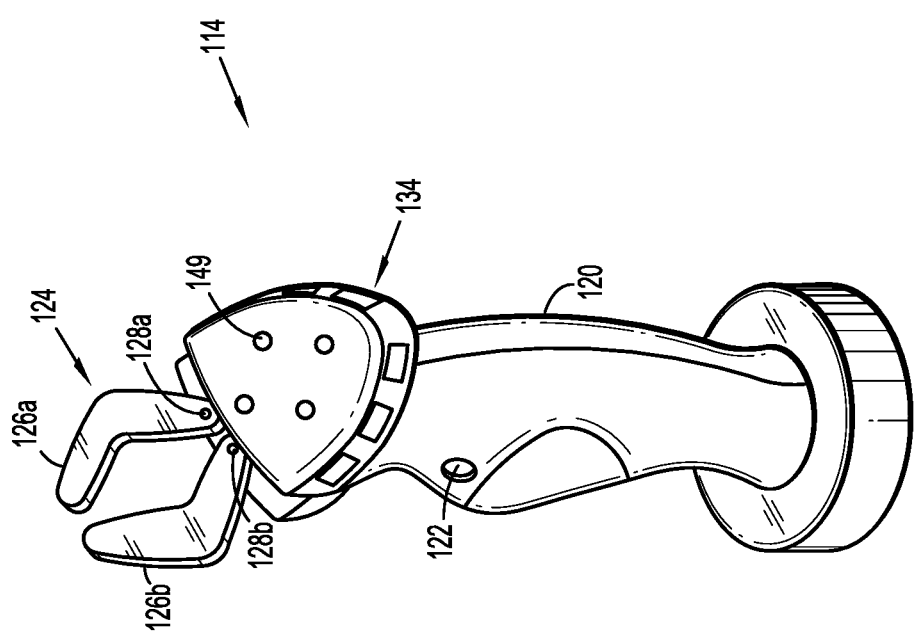
FIG. 2 is an illustration of a handpiece shown in accordance with an embodiment of the present disclosure.
Figure 3:
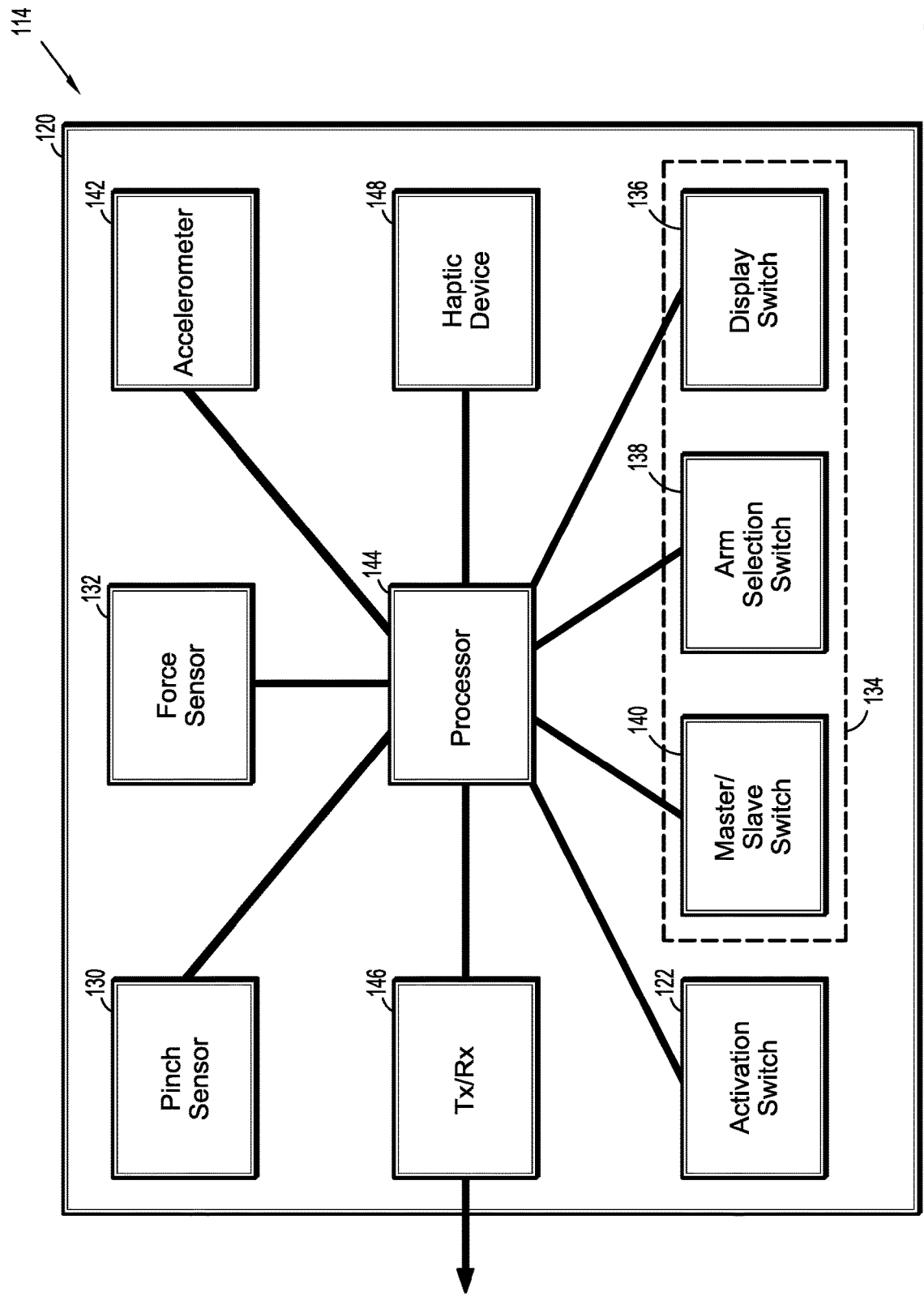
FIG. 3 is a schematic illustration of the handpiece of FIG. 2.

FIGS. 2 and 3 illustrate one example of the handpiece 114 for use in the embodiments described herein. The handpiece 114 may have an ergonomic design to reduce any fatigue experienced by the clinician. The handpiece 114 includes a housing 120 configured to house the various components of the handpiece 114. An activation switch 122 is used to activate the robotic surgical device 102. A pinch interface 124 includes pair of pinch members 126a, 126b that pivot about points 128a, 128b, respectively. Each of the pinch members 126a, 126b included a pinch sensor 130 that determines the relative distance between the pinch members 126a, 126b. The jaw members of the end effector 106 are controlled to open or close based on the determined relative distance of pinch members 126a, 126b. Once the pinch members 126a, 126b reach their respective movement limits, a force sensor 132 determines the amount of force being applied to the pinch members 126a, 126b. The amount of force being applied is multiplied by a factor and translated as a closure force for the jaw members of the end effector 106. In other embodiments, activation of a stapling or vessel sealing procedure may apply a predetermined closure force for the jaw members of the end effector 106.

The handpiece 114 also includes one or more function switches 134. The handpiece 114 may include a display switch 136. When the clinician activates the display switch 136, the clinician may use the handpiece 114 to control the display 112. For example, the clinician may move a cursor, zoom in or out, select areas, or any other function that may be performed on the display 112. Because the robotic surgical device 102 has a plurality of arms 104, the clinician may use an arm selection switch 138 to select one of the arms 104 of robotic surgical device 102. Upon selection of one of the arms 104, movement of the handpiece 114 causes movement of the selected arm 104. The present robotic surgical device may also include a master/slave configuration where the robotic surgical device includes a number of master devices and each master device includes a corresponding number of slave devices. A master/slave switch 140 may be used to select the various master and slave devices. The handpiece 114 is the master and the arms 104 are the slaves.

The handpiece 114 also includes an accelerometer 142 for measuring proper acceleration, which is the acceleration relative to a free-fall, or inertial, observer who is momentarily at rest relative to the object being measured. Specifically, the accelerometer 142 may be a single-axis or multi-axis accelerometer that may detect magnitude and direction of the proper acceleration (or g-force), as a vector quantity. The accelerometer 142 may also sense rotational acceleration, coordinate acceleration, vibration, or shock of handpiece 114.

A processor 144 receives signals from activation switch 122, pinch sensor 130, force sensor 132, function switches 134, and accelerometer 142 and transmits the signals by conventional means via a transceiver 146 to the controller 110. The transceiver 146 may also receive a signal from controller 110 to provide a haptic feedback to the clinician via a haptic device 148 provided on handpiece 114. The haptic device 148 may be any device that provides a simulated tactile response to the clinician.

The handpiece 114 also includes a plurality of optical markers 149. The optical markers 149 are arranged in a pattern (e.g., a diamond pattern as shown in FIG. 2) in order to provide a distance and an orientation of the handpiece 114 as will be described below. Any number of optical markers 149 may be used and the optical markers 149 may be arranged in any pattern.

Figure 4:
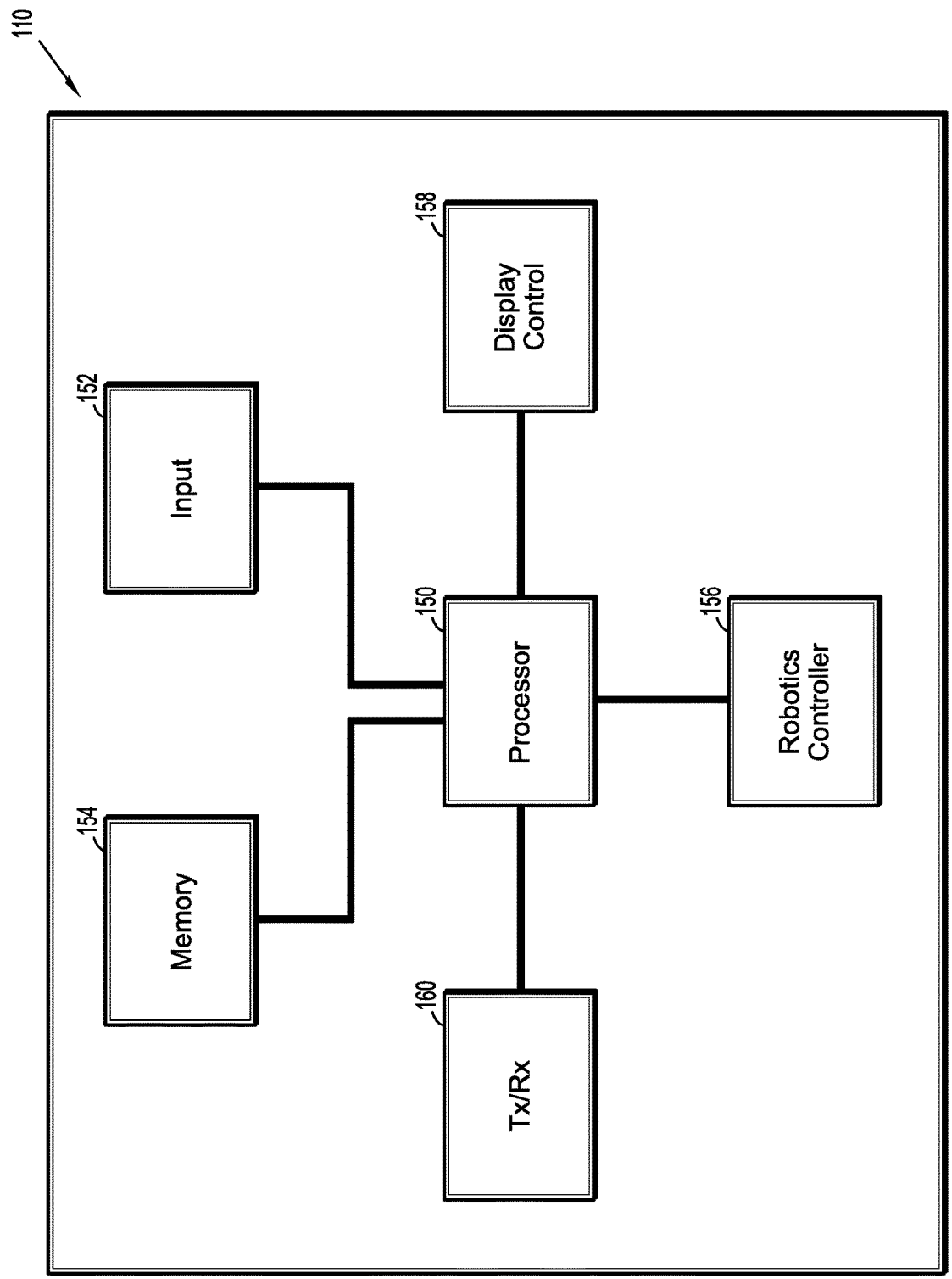
FIG. 4 is a schematic illustration of a controller in accordance with an embodiment of the present disclosure.

FIG. 4 is a schematic block diagram of the controller 110 of FIG. 1. The controller 110 includes a processor 150, an input 152, a memory 154, a robotics controller 156, a display control 158, and a transceiver 160. The processor 150 may be an integrated circuit or a circuit composed of analog or digital components that receives information or data and processes the received information or data to provide an output. For example, the processor 150 may integrate acceleration sensor signals from accelerometer 142 to determine orthogonal and rotational movement or position. The input 152, which may be one or more switches, a keyboard, mouse, a touch screen, etc., is operated by the clinician to perform various functions. The memory 154 may store algorithms that are used by the processor to control various aspects of the robotic surgical system 100. The memory 154 may also store images related to a patient or a database of optical marker patterns to determine the distance and orientation of the handpiece 114. The robotics controller 156 receives signals from the processor 150 to control movement of the robotic surgical devices 102. The display control 158 receives data from the processor 150 and renders an image that is provided to the display 112. The transceiver 160 receives data from the handpiece 114. That data is used by the processor 150 to control the robotic surgical device 102 or the display 112.

Figure 5:
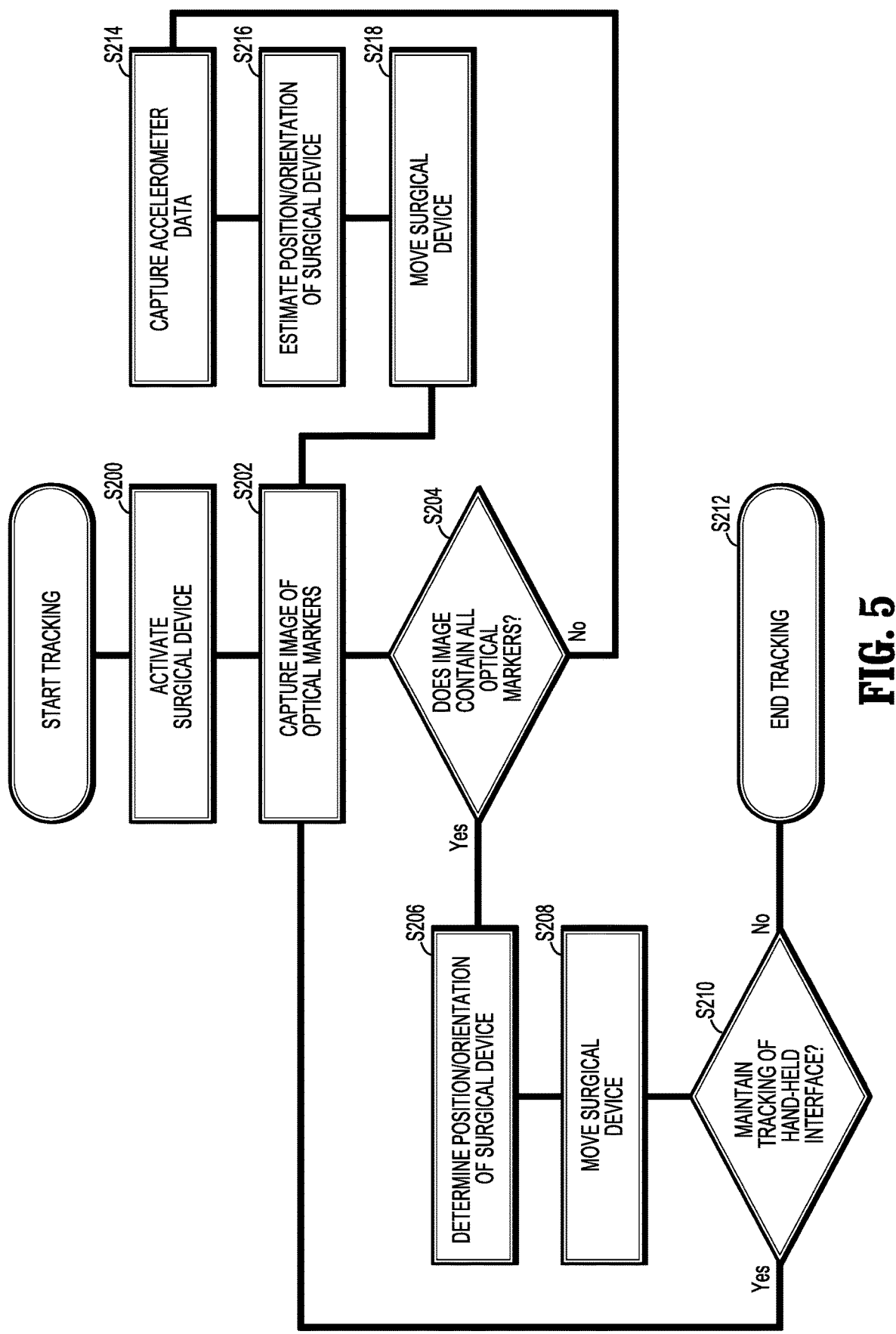
FIG. 5 is a flowchart depicting a tracking algorithm in accordance with an embodiment of the present disclosure.

FIG. 5, which will be discussed in conjunction with FIGS. 1-4, is a flowchart depicting a tracking method of the handpiece 114 in accordance with an embodiment of the present disclosure. As shown in FIG. 5, the robotic surgical device 102 is activated in step s200. The OMS 118 captures an image of the optical markers 149 in step s202. After the OMS 118 captures the image, the image is processed by the processor 150 to determine if the image includes all of the optical markers 149. If the captured image includes all of the optical markers 149, the process proceeds to step s206 where the position or orientation of the surgical device is determined. The memory 154 stores a lookup table where two or more optical marker pattern images are associated with a distance and orientation. In step s206, the processor 150 compares the captured image to the images of optical marker patterns stored in memory 154. The processor then determines which of the stored images best matches that captured image. The processor 150 then reads the lookup table to extract the distance and orientation of the handpiece 114. In other embodiments, the distance or angles between optical markers can be calculated to determine the distance and orientation of the handpiece 114. The distance and orientation of the handpiece 114 is translated by the processor 150 to determine the desired position and orientation of the robotic surgical device 102 or the end effectors 106. Then in step s208, the robotic surgical device 102 or the end effectors 106 are moved based on the determined position or orientation. In step s210, the processor 150 determines whether it should continue tracking the handpiece 114. If the handpiece 114 is no longer needed, the process proceeds to step s212 where tracking is discontinued. If the handpiece 114 is still needed, the process proceeds to step s202.

In step s204, if the captured image does not contain all of the optical markers 149, the acceleration of the handpiece 114 is captured by the accelerometer 142 in step s214. The accelerometer 142 measures the magnitude and direction of movement of the handpiece 114 as well as senses the orientation of the handpiece 114. The magnitude and direction or the orientation of the handpiece 114 is provided to the processor 150 to estimate the desired position or orientation of the robotic surgical device 102 or the end effectors 106 in step s216. The robotic surgical device 102 or end effectors 106 are then moved based on the estimated position or orientation in step s218.

Figure 6:
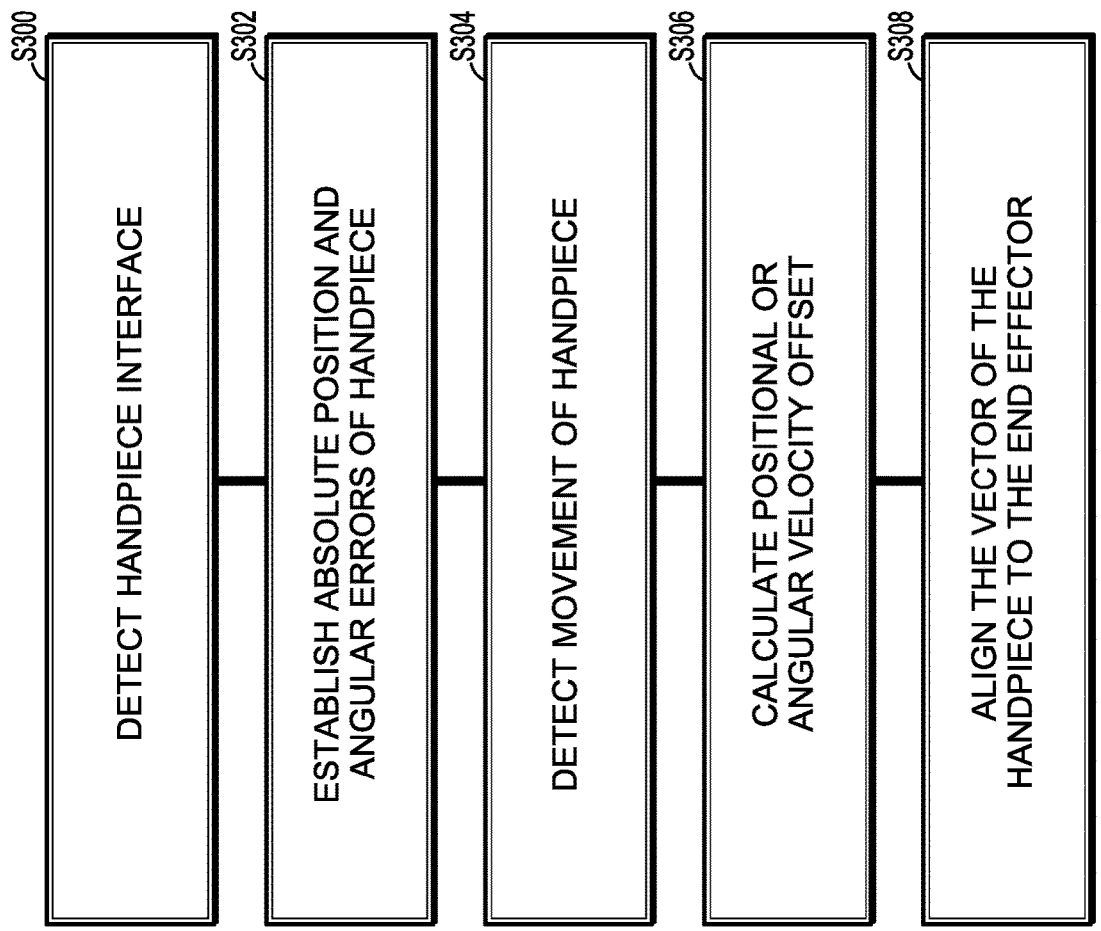
FIG. 6 is a flowchart depicting an alignment algorithm in accordance with an embodiment of the present disclosure.

Because the accelerometer 142 of the handpiece 114 lacks a true reference to determine the position or orientation and the potential of drift relative to the patient, the processor 150 executes an alignment algorithm stored in memory 154. The alignment algorithm reestablishes an absolute orientation of the handpiece 114 with the robotic surgical device 102, the robotic arms 104, the end effectors 106, the surgical field, or the patient without any disorientating jumps by adjusting the non-zero velocities to bring the computed handpiece 114 position back in absolute orientation with the optical tracking system. The system will not make corrections when movement of the handpiece 114 is approaching zero velocity. As shown in FIG. 6, the algorithm starts in step s300 where the handpiece 114 is detected. In step s302, the absolute position and angular errors of the handpiece 114 are established by reverse calculating the location of the handpiece 114 with respect to the robots current position and determining the current offset from the position of the handpiece 114 with respect to the robots current position and the position of the handpiece 114 in the optical field. In step s304, movement of the handpiece 114 is detected by the processor 150. For example, when the handpiece 114 is moved, the accelerometer 142 transmits acceleration data to the processor 150. Based on the acceleration data, the processor 150 determines that the handpiece 114 is moving.

The processor 150 then calculates the positional or angular velocity offset needed to bring the vector of the handpiece 114 into alignment with the current vector of movement relative to the robotic surgical device 102, the robotic arms 104, or the end effectors 106 in step s306. The positional or angular velocity offset is a fractional multiplier of the velocity of the handpiece 114. The magnitude of the fractional multiplier is derived from the magnitude of the offset in the orientation of the movement of the handpiece 114 and a scale factor. The scaling factor may be a non-dimensional factor, an angular factor, a dimensional factor, or a time factor.

For example, in a given system where the device, e.g., the end effectors 106, are mathematically located as a vector reference from a x, y, z coordinate positioned within an overall coordinate position and the vector of the handpiece 114 has drifted angularly while the clinician moves the handpiece 114 in a rotation about the y-axis, the magnitude of the fractional multiplier can be calculated as follows:

$$\dot{\omega}_{Y_{ROBOT}} = \dot{\omega}_{Y_{Handpiece}} + \lfloor \dot{\omega}_{Y_{Handpiece}} \times (\omega_{Y_{Handpiece}} - \omega_{Y_{ROBOT}}) \times \text{ScaleFactor} \rfloor \quad \text{(Eq. 1)},$$

where $\omega$ is the angular position and $\dot{\omega}$ is the angular velocity.

In the alignment algorithm, the larger the inverse time constant (scale factor), the faster the alignment occurs. This results in a correction that is asymptotic to the fully aligned condition in which the offset between the velocity of the handpiece 114 and the velocity of the robotic surgical device 102, the robotic arms 104, or the end effectors 106 approach equality as the required correction approaches zero regardless of the magnitude of the scale factor.

In other embodiments, the velocity offset may be constant as long as the velocity along the calculated offset exists and the error is greater than zero (0). In such situations, the inverse time constant should be relatively small in order to maintain the desired subtleness of the alignment process. There may be no correction when the velocity is zero to prevent unintentional movement and eliminate any disorienting affects due to mismatched motions between the user and the robot.

Once the positional or angular velocity offset is calculated in step s306, the vector of the handpiece 114 is aligned to the vector of the robotic surgical device 102, the robotic arms 104, or the end effectors 106.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing FIGS. are presented only to demonstrate certain examples of the disclosure. Other elements, steps, methods and techniques that are insubstantially different from those described above and/or in the appended claims are also intended to be within the scope of the disclosure.

What is claimed is:

1. A robotic surgical system comprising:
   a robotic surgical device including:
     at least one robotic arm; and
     an end effector having a pair of jaw members at a distal end of the robotic arm;
   at least one handpiece, the handpiece including:
     a housing;
     a pinch interface supported on the housing and being configured to control the end effector on the robotic surgical device, the pinch interface including a pair of pinch members each independently pivotally connected to the housing about a respective pivot point, wherein the pivot points are spaced a distance apart from one another;
     an activation switch configured to control activation of the robotic surgical device;
     at least one marker;
     an accelerometer configured to measure acceleration of the handpiece; and
     a transmitter configured to transmit data from at least one of the pinch interface, each pinch member, or accelerometer to the robotic surgical device;
   a tracking system configured to track the at least one marker and provide a position or orientation of the handpiece; and
   a controller configured to receive data indicative of: (i) the position of the handpiece from the tracking system (ii) the measured acceleration of the handpiece from the accelerometer, and integrate the measured acceleration to establish a second position beyond that of the tracking system, the controller being configured to control movement of the robotic arm based on the position or the measured acceleration of the handpiece.

2. The robotic surgical system of claim 1, wherein the pair of pinch members include at least one pinch sensor configured to measure relative movement of the pair of pinch members.

3. The robotic surgical system of claim 2, wherein the relative movement of the pair of pinch members causes the pair of jaw members to move.

4. The robotic surgical system of claim 3, wherein the measured relative movement of the pair of pinch members is multiplied by a predetermined factor to cause movement of the pair of jaw members.

5. The robotic surgical system of claim 1, wherein the pair of pinch members include a force sensor configured to measure a force applied to the pair of pinch members.

6. The robotic surgical system of claim 5, the force applied to the pair of pinch members causes the pair of jaw members to move to a position at which a closure force to tissue disposed between the pair of jaw members is proportionally matched to the pinch members.

7. The robotic surgical system of claim 1, wherein the robotic surgical device includes a plurality of robotic arms and wherein the activation switch is configured to select one of the plurality of robotic arms.

8. The robotic surgical system of claim 1 where the tracking system is an optical, a magnetic, or an inductive tracking system.

9. A hand-held instrument for controlling a robotic surgical device, the hand-held instrument comprising:
   at least one handpiece, the handpiece including:
     a housing;
     a pinch interface supported on the housing and being configured to control an end effector on a robotic surgical device, the pinch interface including a pair of pinch members each independently pivotally connected to the housing about a respective pivot point, wherein the pivot points are spaced a distance apart from one another;
     an activation switch configured to control activation of the robotic surgical device;
     an accelerometer configured to measure acceleration of the handpiece; and
     a transmitter configured to transmit data from at least one of the pinch interface, each pinch member, or the accelerometer to a robotic surgical device to control movement of a robotic surgical device.

10. A method for controlling a robotic surgical device using a hand-held interface, the method comprising:
    actuating an activation switch of the hand-held interface to activate the robotic surgical device;
    capturing an image of a plurality of optical markers on the hand-held interface;
    determining a position or orientation of the hand-held interface based on the image;
    receiving acceleration data from the hand-held interface; and
    controlling movement of the robotic surgical device based on the determined position or orientation of the hand-held interface or the acceleration data of the hand-held interface.

11. The method of claim 10, wherein a position or orientation of the robotic surgical device is controlled based on the determined position or orientation of the hand-held interface.

12. The method of claim 11, wherein the position or orientation of the robotic surgical device is controlled based on the acceleration data when the position and orientation of the hand-held interface can not be determined.

13. The method of claim 12, wherein the acceleration data is used to calculate an estimated position or orientation of the robotic surgical device.

14. The method of claim 10, wherein determining the position or orientation of the hand-held interface includes comparing the captured image to a database of images.

15. The method of claim 10, wherein determining the position or orientation of the hand-held device includes calculating a plurality of distances between the plurality of optical markers.

16. The method of claim 10, wherein the position of the hand-held interface is brought into alignment when the hand-held interface is locatable by the optical markers by adjusting a non-zero velocity movement of the robot.

* * * * *